US012773353B2

(12) United States Patent
Sherman et al.

(10) Patent No.: US 12,773,353 B2
(45) Date of Patent: Oct. 27, 2026

(54) MEDICAL TAPES WITH HIGH OPTICAL CLARITY WHEN OVER-TAPED

(71) Applicant: Solventum Intellectual Properties Company, Maplewood, MN (US)

(72) Inventors: Audrey A. Sherman, Woodbury, MN (US); John J. Rogers, St. Paul, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 1196 days.

(21) Appl. No.: 17/770,375

(22) PCT Filed: Nov. 19, 2020

(86) PCT No.: PCT/IB2020/060937

§ 371 (c)(1),
(2) Date: Apr. 20, 2022

(87) PCT Pub. No.: WO2021/099997

PCT Pub. Date: May 27, 2021

(65) Prior Publication Data

US 2022/0387226 A1 Dec. 8, 2022

Related U.S. Application Data

(60) Provisional application No. 62/937,914, filed on Nov. 20, 2019.

(51) Int. Cl.
*A61F 13/02* (2024.01)
*A61F 13/0246* (2024.01)

(52) U.S. Cl.
CPC ...... *A61F 13/0269* (2013.01); *A61F 13/0253* (2013.01)

(58) Field of Classification Search
None
See application file for complete search history.

(56) References Cited

U.S. PATENT DOCUMENTS

RE24,986 E 5/1961 Stephenson
3,389,827 A 6/1968 Abere et al.
3,645,835 A 2/1972 Hodgson
3,786,116 A 1/1974 Milkovich et al.
3,842,059 A 10/1974 Milkovich et al.
(Continued)

FOREIGN PATENT DOCUMENTS

CN 106102670 B 1/2020
WO 1996034028 A1 10/1996
(Continued)

OTHER PUBLICATIONS

International Search Report for PCT International Application No. PCT/IB2020/060937, mailed on Feb. 11, 2021, 6 pages.
(Continued)

*Primary Examiner* — Arti Singh-Pandey

(57) ABSTRACT

Medical tapes include an optically transparent tape backing and an optically transparent adhesive layer, typically a pressure sensitive adhesive, disposed on the backing The tape is optically transparent and has a moisture vapor transmission rate (MVTR) of at least 250 g/m$^2$/24 hrs/37° C./100-10% RH using the inverted cup method. The tape remains optically transparent when over-taped, such that a multi-layer tape stack of at least 2 layers of tape are formed.

8 Claims, 3 Drawing Sheets

(56) References Cited

U.S. PATENT DOCUMENTS

| | | | |
|---|---|---|---|
| 4,112,213 | A | 9/1978 | Waldman |
| 4,279,717 | A | 7/1981 | Eckberg et al. |
| 4,310,509 | A | 1/1982 | Berglund et al. |
| 4,313,988 | A | 2/1982 | Koshar et al. |
| 4,323,557 | A | 4/1982 | Rosso et al. |
| 4,421,904 | A | 12/1983 | Eckberg et al. |
| 4,595,001 | A | 6/1986 | Potter et al. |
| 4,693,935 | A | 9/1987 | Mazurek |
| 4,737,410 | A | 4/1988 | Kantner |
| 4,900,474 | A | 2/1990 | Terae et al. |
| 4,941,882 | A | 7/1990 | Ward et al. |
| 5,028,679 | A | 7/1991 | Terae et al. |
| 5,118,775 | A | 6/1992 | Inomata et al. |
| 5,160,315 | A | 11/1992 | Heinecke et al. |
| 5,214,119 | A | 5/1993 | Leir et al. |
| 5,236,997 | A | 8/1993 | Fujiki |
| 5,461,134 | A | 10/1995 | Leir et al. |
| 5,512,650 | A | 4/1996 | Leir et al. |
| 5,527,578 | A | 6/1996 | Mazurek et al. |
| 5,637,646 | A | 6/1997 | Ellis |
| 5,858,545 | A | 1/1999 | Everaerts et al. |
| 6,007,914 | A | 12/1999 | Joseph et al. |
| 6,294,249 | B1 | 9/2001 | Hamer et al. |
| 6,461,467 | B2 | 10/2002 | Blatchford et al. |
| 7,153,924 | B2 | 12/2006 | Kuepfer et al. |
| 8,765,881 | B2 | 7/2014 | Hays et al. |
| 2001/0051178 | A1 | 12/2001 | Blatchford et al. |
| 2004/0184150 | A1 | 9/2004 | Johnson et al. |
| 2007/0148475 | A1 | 6/2007 | Sherman et al. |
| 2011/0212325 | A1 | 9/2011 | Determan et al. |
| 2011/0300296 | A1 | 12/2011 | Sherman et al. |
| 2015/0238444 | A1 | 8/2015 | Menon et al. |
| 2017/0065459 | A1 | 3/2017 | Ragg |
| 2018/0280591 | A1 | 10/2018 | Menon et al. |

FOREIGN PATENT DOCUMENTS

| | | | |
|---|---|---|---|
| WO | 1996034030 | A1 | 10/1996 |
| WO | 1996035458 | A2 | 11/1996 |
| WO | 1997040103 | A1 | 10/1997 |
| WO | 1998017726 | A1 | 4/1998 |
| WO | 2000002966 | A1 | 1/2000 |
| WO | 2009014881 | A2 | 1/2009 |
| WO | 2015100319 | A1 | 7/2015 |
| WO | 2016105501 | A1 | 6/2016 |

OTHER PUBLICATIONS

Lochmann, “Metalloesters, 11 a), Disproportionation” of Living (Lithiated) Oligomers of Methyl Methacrylate, Macromolecular Chemistry and Physics, 1984, vol. 185, No. 09, pp. 1819-1826.

Song, “Functional Polymers. 31. ESCA Spectroscopy of Polyesters Stabilized with Polymer Bound Ultraviolet Stabilizers”, Polymer Bulletin, 1984, vol. 12, pp. 245-251.

“Opsite Flexigrid Application,” YouTube, [retrieved from the Internet on Jan. 26, 2021], URL https://www.youtube.com/watch^v=IHFgvMb-5UM, 2015, pp. 1-3, XP054981340.

“Opsite-Post-Op Visible Drain Dressing,” Smith Nephew, [retrieved from the Internet on Jan. 26, 2021], URL: <https://web.archive.org/web/20181129185007/https://www.smith-nephew.com/key-products/advanced-wound-management/opsite-post-op/opsite-post-op-visible-drain-dressing/>, 2018, pp. 1-3, XP055768731.

MEDICAL TAPES WITH HIGH OPTICAL CLARITY WHEN OVER-TAPED

FIELD OF THE DISCLOSURE

This disclosure relates to tapes, especially tapes for medical uses that are optically transparent and remain transparent even when over-taped.

BACKGROUND

A wide range of adhesive articles are used in medical applications. These adhesive articles include gels used to attach electrodes and other sensing devices to the skin of a patient, a wide range of tapes to secure medical devices to a patient, and adhesive dressings used to cover and protect wounds.

Many of the adhesive articles use pressure sensitive adhesives. Pressure sensitive adhesives are well known to one of ordinary skill in the art to possess certain properties at room temperature including the following: (1) aggressive and permanent tack, (2) adherence with no more than finger pressure, (3) sufficient ability to hold onto an adherend, and (4) sufficient cohesive strength to be removed cleanly from the adherend. Materials that have been found to function well as pressure sensitive adhesives are polymers designed and formulated to exhibit the requisite viscoelastic properties resulting in a desired balance of tack, peel adhesion, and shear strength. The most commonly used polymers for preparation of pressure sensitive adhesives are natural rubber, synthetic rubbers (e.g., styrene/butadiene copolymers (SBR) and styrene/isoprene/styrene (SIS) block copolymers), various (meth)acrylate (e.g., acrylate and methacrylate) copolymers, and silicones.

SUMMARY

This disclosure relates to tapes, especially tapes for medical uses that are optically transparent and remain transparent even when over-taped. In some embodiments, the tape comprises an optically transparent tape backing with a first major surface and a second major surface, and an optically transparent pressure sensitive adhesive layer with a first major surface and a second major surface, where at least a portion of the second major surface of the optically transparent pressure sensitive layer is adjacent to at least a portion of the first major surface of the optically transparent tape backing. In some embodiments, the tape is optically transparent and has a moisture vapor transmission rate (MVTR) of at least 250 $g/m^2/24$ hrs/37° C./100-10% RH using the inverted cup method. The tape is capable of forming an optically transparent multi-layer tape stack comprising at least 2 layers of tape.

Also disclosed are multi-layer articles comprising a substrate surface, typically mammalian skin, and a multi-layer tape stack disposed on the substrate surface, where the multi-layer tape stack comprises at least 2 layers of the optically transparent tape described above. The multi-layer tape stack is optically transparent.

Also disclosed are methods of adhering medical devices to mammalian skin. In some embodiments the method comprises providing a substrate surface comprising mammalian skin, providing a medical device to be adhered to the mammalian skin, placing the medical device adjacent to substrate surface, contacting a first portion of the optically transparent tape described above to the medical device and to a portion of the substrate surface, and contacting a second portion of the optically transparent tape to the first portion of optically transparent tape, to form a tape stack of optically transparent tape, wherein the tape stack is optically transparent.

BRIEF DESCRIPTION OF THE DRAWINGS

The present application may be more completely understood in consideration of the following detailed description of various embodiments of the disclosure in connection with the accompanying drawings.

Figure 1:
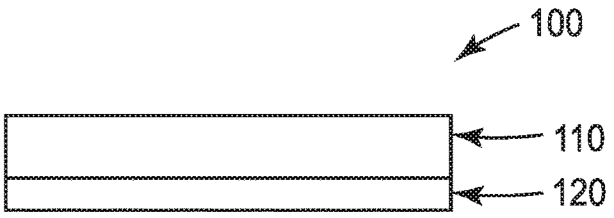
FIG. 1 is a cross-sectional view of a tape article of this disclosure.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present disclosure. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

The use of adhesive products in the medical industry has long been prevalent and is increasing. However, while adhesives and adhesive articles have shown themselves to be very useful for medical applications, there are also issues in the use of adhesives and adhesive articles. While many medical adhesive articles are directly applied to wound areas, a wide range of medical articles, such as tapes and drapes, are not applied to the wound area itself but rather play a supporting role to treatment such as holding absorbent materials or medical devices in place on the skin. Examples of medical devices that are held in place with tapes include drapes, tubing, catheters, ostomy appliances, and sensors. Additional uses for medical tapes include a wide variety of applications where tape is applied to the skin of a patient. Examples include holding a patient to an operating or treatment table, covering a part of a patient such as holding eyes closed during surgery, or immobilizing a hand during surgery to the hand, or to overlay a wound closure, not as a wound dressing but to hold the wound closed especially when the wound is closed with staples or sutures.

Medical adhesives have a wide array of desired properties. Among these properties are the typical adhesive requisites of sufficient peel adhesion and shear holding power, as well as flexibility so as to bend with the body, a high moisture vapor transmission rate (MVTR) and low medical adhesive-related skin injury (MARSI).

MVTR is a measure of the passage of water vapor through a substance or barrier. Because perspiration naturally occurs on the skin, if the MVTR of a material or adhesive system is low, this can result in moisture accumulation between the skin and the adhesive that can cause the adhesive to "float off" or peel away and also can promote other detrimental effects such as bacterial growth and skin irritation. Therefore, much work has focused upon the development of adhesive systems that have a high MVTR.

Medical adhesive-related skin injury (MARSI) has a significant negative impact on patient safety. Skin injury related to medical adhesive usage is a prevalent but under recognized complication that occurs across all care settings and among all age groups. In addition, treating skin damage is costly in terms of service provision, time, and additional treatments and supplies.

Skin Injury occurs when the superficial layers of the skin are removed along with the medical adhesive product, which not only affects skin integrity but can cause pain and the risk of infection, increase wound size, and delay healing, all of which reduce patients' quality of life.

Medical adhesive tape can be simply defined as a pressure-sensitive adhesive and a backing that acts as a carrier for the adhesive. The US Food and Drug Administration more specifically defines a medical adhesive tape or adhesive bandage as "a device intended for medical purposes that consists of a strip of fabric material or plastic, coated on one side with an adhesive, and may include a pad of surgical dressing without a disinfectant. The device is used to cover and protect wounds, to hold together the skin edges of a wound, to support an injured part of the body, or to secure objects to the skin."

While the pathophysiology of MARSI is only partially understood. Skin injury results when the skin to adhesive attachment is stronger than skin cell to skin cell attachment. When adhesive strength exceeds the strength of skin cell to skin cell interactions, cohesive failure occurs within the skin cell layer.

In addition to these already difficult to achieve properties additional requirements are desired, including optical properties, such as optical transparency to permit one to see through the adhesive article. Increasingly, optical properties of medical adhesive tapes have become more important. In U.S. Pat. No. 6,461,467, the term "substantially contact transparent" is used to describe their articles and meaning that when adhered to a patient's skin, a wound or catheter site can be visually monitored through those portions of the backing and pressure sensitive adhesive or adhesives in contact with the patient's skin without requiring removal of the dressing.

An issue with transparent medical tapes that has not been described is the affect over-taping can have on the properties of the tape. These issues come about because frequently one wishes to over-tape the medical tape. By this it is meant that more than one layer of tape is applied, where the second layer is adhered to at least a portion of the backside of the first layer of tape. The over-taping may involve the second tape layer directly covering the first tape layer, or it may be in a variety of patterns such as an X-shape where the center of the X is attached to a medical device that is desired to be secured to the patient. Even if each tape has some level of transparency, upon over-taping the transparency can be lost.

As multiple layers of tape are over-taped, optical properties are affected. One effect is that the multi-layer articles are thicker and therefore the absorption and light scattering caused by the single layer of tape is increased when another layer of tape is added to form the multi-layer article.

Optical properties in multi-layer articles are further complicated because with each added layer, a new interface is generated. Whenever an interface is present the possibility of optical interference is present. A frequent issue is refraction when a visible light ray encounters the interface, when the materials that form the interface have different indices of refraction. This phenomenon is described by Snell's Law. A commonly observed example of this phenomenon is encountered by the air/water interface. If one places an object, like a canoe paddle in the water, the paddle appears to be bent, as a result of the refraction of visible light. It is generally suitable to select materials that have refractive indices that are similar such that there is not a large difference in refractive indices at the interface between layers.

Disclosed herein are transparent medical tapes that are capable of being over-taped and retain their transparency. Optical transparency in the context of these tapes and over-taped articles is further defined below. Over-taped articles are also disclosed comprising a substrate surface, such as mammalian skin, and a multi-layer article disposed on the substrate surface where the multi-layer article comprises over-taped layers. Also disclosed are methods of adhering a medical device to a substrate surface by over-taping.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. For example, reference to "a layer" encompasses embodiments having one, two or more layers. As used in this specification and the appended claims, the term "or" is generally employed in its sense including "and/or" unless the content clearly dictates otherwise.

The term "adhesive" as used herein refers to polymeric compositions useful to adhere together two adherends. Examples of adhesives are pressure sensitive adhesives and gel adhesives.

Pressure sensitive adhesive compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process.

As used herein, the term "gel adhesive" refers to a tacky semi-solid crosslinked matrix containing a liquid or a fluid that is capable of adhering to one or more substrates. The gel adhesives may have some properties in common with pressure sensitive adhesives, but they are not pressure sensitive adhesives.

The terms "Tg" and "glass transition temperature" are used interchangeably. If measured, Tg values are determined by Differential Scanning calorimetry (DSC) at a scan rate of 10° C./minute, unless otherwise indicated. Typically, Tg values for copolymers are not measured but are calculated using the well-known Fox Equation, using the monomer Tg values provided by the monomer supplier, as is understood by one of skill in the art.

The term "room temperature" refers to ambient temperature, generally 20-22° C., unless otherwise noted.

The term "(meth)acrylate" refers to monomeric acrylic or methacrylic esters of alcohols. Acrylate and methacrylate monomers or oligomers are referred to collectively herein as "(meth)acrylates". Polymers described as "(meth)acrylate-based" are polymers or copolymers prepared primarily (greater than 50% by weight) from (meth)acrylate monomers and may include additional ethylenically unsaturated monomers.

The terms "siloxane-based" as used herein refer to polymers or units of polymers that contain siloxane units. The terms silicone or siloxane are used interchangeably and refer to units with dialkyl or diaryl siloxane (—$SiR_2O$—) repeating units.

The term "adjacent" as used herein when referring to two layers means that the two layers are in proximity with one another with no intervening open space between them. They may be in direct contact with one another (e.g. laminated together) or there may be intervening layers.

The terms "polymer" and "macromolecule" are used herein consistent with their common usage in chemistry. Polymers and macromolecules are composed of many repeated subunits. As used herein, the term "macromolecule" is used to describe a group attached to a monomer that has multiple repeating units. The term "polymer" is used to describe the resultant material formed from a polymerization reaction.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The term "aralkylene" refers to a divalent group of formula —$R^a$-$Ar^a$— where IV is an alkylene and $Ar^a$ is an arylene (i.e., an alkylene is bonded to an arylene).

The term "heteroalkylene" refers to a divalent group that includes at least two alkylene groups connected by a thio, oxy, or —NR— where R is alkyl. The heteroalkylene can be linear, branched, cyclic, substituted with alkyl groups, or combinations thereof. Some heteroalkylenes are poloxyyalkylenes where the heteroatom is oxygen such as for example, —$CH_2CH_2(OCH_2CH_2)_nOCH_2CH_2$—.

Disclosed herein are optically transparent tapes comprising an optically transparent tape backing with a first major surface and a second major surface and an optically transparent pressure sensitive adhesive layer with a first major surface and a second major surface, wherein at least a portion of the second major surface of the optically transparent pressure sensitive adhesive layer is adjacent to at least a portion of the first major surface of the optically transparent tape backing. In some embodiments, the optically transparent pressure sensitive adhesive is disposed on the optically transparent tape backing. The tape has a range of desirable properties, being flexible, being optically transparent, has a moisture vapor transmission rate (MVTR) of at least 250 g/$m^2$/24 hrs/37° C./100-10% RH using the inverted cup method, and is capable of forming an optically transparent multi-layer tape stack comprising at least 2 layers of tape. The tape stack is formed by over-taping the optically transparent tape with another second piece of the optically transparent tape. The over-taping may involve over-taping a portion of the surface of the first tape or it may comprise over-taping the entire surface of the first tape.

As used herein, the term optically transparent refers to an article, film, or adhesive that one can view an object through with the naked eye without the object being distorted or obscured. The current tapes are optically transparent, meaning, in general, that they have a % Transmission (% T) over at least a portion of the visible light spectrum (about 400 to about 700 nm) of at least 85%, a haze of less than 40%, and clarity of at least 50%.

What was discovered is that the tapes of the current disclosure retain their optical properties upon over-taping. The tapes retain their transparency such that a two-layer stack while having a lower % Transmission, a higher haze and a lower clarity than a single layer of the tape, the properties are such that it is possible to clearly view through the two layers of tape. In some embodiments, the two-layer stack has a % T of at least 80%, a haze of less than 70%, and a clarity of at least 30%.

To further clarify the optical properties, in general terms the optical properties can be described in the following general terms:

% Transmission, as the term implies, is a measure of the amount of light transmitted, i.e. to the ratio of the incident light to the output light for an optical object.

Haze is the measurement of wide-angle scattering and causes a loss of contrast or a milky appearance.

Clarity is the measure of narrow-angle scattering and causes the detail of an object to be compromised when viewing it though the substrate. Clarity is also distance-dependent, which means that the farther the object is being viewed through the substrate, the worse its detail becomes.

The higher the haze and the lower the clarity, the more diffusion is occurring. While haze and clarity do not reduce or affect transmission of light, the resulting diffusion can lead to visual aberrations and discrepancies.

In some embodiments, the tape stack may comprise more than 2 layers of optically transparent tape. In some embodiments, the tape stack comprises 3 layers of optically transparent tape, 4 layers so of optically transparent tape or even more.

Moisture vapor transmission rate can be measured in a variety of ways. Typically, the optically transparent tape transmits moisture vapor at a rate of at least 250 g/$m^2$/24 hrs/37° C./100-10% RH, more desirably at least 700 g/$m^2$/24 hrs/37° C./100-10% RH, and most desirably at least 2000 g/$m^2$/24 hrs/37° C./100-10% RH using the inverted cup method as described in U.S. Pat. No. 4,595,001.

The backing is typically a thin-film material (single layer or multilayer). Typically, the thin film material provides resistance against incoming water and contaminants and has a high moisture vapor permeability to allow moisture vapor from the underlying skin to exit. One example of a suitable material is a high moisture vapor permeable film such as described in U.S. Pat. Nos. 3,645,835 and 4,595,001 which describe methods of making such films and methods for testing their permeability.

The backing is generally flexible, meaning that it is conformable to anatomical surfaces. As such, when applied to an anatomical surface, it conforms to the surface even when the surface is moved and can stretch and retract. In some embodiments, the backing is an elastomeric polyolefin, polyurethane, polyester, or polyether block amide film. These films combine the desirable properties of resiliency, high moisture vapor permeability, and transparency. An example of a material suitable for the backing is in 3M TEGADERM IV Dressings available from 3M Company. Other suitable materials include polyesters such as PET (polyethylene terephthalate) and BOPP (biaxially oriented polypropylene). An example of a BOPP film is SBOPP (simultaneous biaxially orientated polypropylene) formed as described in US Patent Publication No. 2004/0184150. In some embodiments, the backing is partially perforated to enhance MVTR.

The pressure sensitive adhesive used in the optically transparent tapes of the current disclosure also has a variety of desirable properties. Typically, the pressure sensitive adhesive comprises a (meth)acrylate-based or silicone-based pressure sensitive adhesive, or an adhesive that is a combination of a (meth)acrylate-based and silicone-based pressure sensitive adhesive. In some embodiments it can comprise a silicone-based gel adhesive. For example, the combination to the pressure sensitive adhesive with the backing to form the tape, the tape transmits moisture vapor at a rate greater to or equal to that of human skin.

Particularly suitable (meth)acrylate-based pressure sensitive adhesives include copolymers derived from: (A) at least one monoethylenically unsaturated alkyl (meth) acrylate monomer (i.e., alkyl acrylate and alkyl methacrylate monomer); and (B) at least one monoethylenically unsaturated free-radically copolymerizable reinforcing monomer. The reinforcing monomer has a homopolymer glass transition temperature (Tg) higher than that of the alkyl (meth)acrylate monomer and is one that increases the glass transition temperature and cohesive strength of the resultant copolymer. Herein, "copolymer" refers to polymers containing two or more different monomers, including terpolymers, tetrapolymers, etc.

Monomer A, which is a monoethylenically unsaturated alkyl acrylate or methacrylate (i.e., (meth)acrylic acid ester), contributes to the flexibility and tack of the copolymer. Generally, monomer A has a homopolymer Tg of no greater than about 0° C. Typically, the alkyl group of the (meth) acrylate has an average of about 4 to about 20 carbon atoms, or an average of about 4 to about 14 carbon atoms. The alkyl group can optionally contain oxygen atoms in the chain thereby forming ethers or alkoxy ethers, for example. Examples of monomer A include, but are not limited to, 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate. Other examples include, but are not limited to, poly-ethoxylated or -propoxylated methoxy (meth)acrylates such as acrylates of CARBOWAX (commercially available from Union Carbide) and NK ester AM90G (commercially available from Shin Nakamura Chemical, Ltd., Japan). Suitable monoethylenically unsaturated (meth)acrylates that can be used as monomer A include isooctyl acrylate, 2-ethyl-hexyl acrylate, and n-butyl acrylate. Combinations of various monomers categorized as an A monomer can be used to make the copolymer.

Monomer B, which is a monoethylenically unsaturated free-radically copolymerizable reinforcing monomer, increases the glass transition temperature and cohesive strength of the copolymer. Generally, monomer B has a homopolymer Tg of at least about 10° C. Typically, monomer B is a reinforcing (meth)acrylic monomer, including an acrylic acid, a methacrylic acid, an acrylamide, or a (meth) acrylate. Examples of monomer B include, but are not limited to, acrylamides, such as acrylamide, methacrylamide, N-methyl acrylamide, N-ethyl acrylamide, N-hydroxyethyl acrylamide, diacetone acrylamide, N,N-dimethyl acrylamide, N, N-diethyl acrylamide, N-ethyl-N-aminoethyl acrylamide, N-ethyl-N— hydroxyethyl acrylamide, N,N-dihydroxyethyl acrylamide, t-butyl acrylamide, N,N-dimethylaminoethyl acrylamide, and N-octyl acrylamide. Other examples of monomer B include itaconic acid, crotonic acid, maleic acid, fumaric acid, 2,2-(diethoxy)ethyl acrylate, 2-hydroxyethyl acrylate or methacrylate, 3-hydroxypropyl acrylate or methacrylate, methyl methacrylate, isobornyl acrylate, 2-(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl formamide, N-vinyl acetamide, N-vinyl pyrrolidone, and N-vinyl caprolactam. Particularly suitable reinforcing acrylic monomers that can be used as monomer B include acrylic acid and acrylamide. Combinations of various reinforcing monoethylenically unsaturated monomers categorized as a B monomer can be used to make the copolymer.

Generally, the (meth)acrylate copolymer is formulated to have a resultant Tg of less than about 0° C. and more typically, less than about −10° C. Such (meth)acrylate copolymers generally include about 60 parts to about 98 parts per hundred of at least one monomer A and about 2 parts to about 40 parts per hundred of at least one monomer B. In some embodiments, the (meth)acrylate copolymers have about 85 parts to about 98 parts per hundred or at least one monomer A and about 2 parts to about 15 parts of at least one monomer B.

Examples of suitable (meth)acrylate-based pressure sensitive adhesives that can be applied to skin are described in U.S. Patent No. RE 24,906. In some embodiments, a 97:3 iso-octyl acrylate:acrylamide copolymer adhesive can be used or a 70:15:15 isooctyl acrylate: ethyleneoxide acrylate: acrylic acid terpolymer, as described in U.S. Pat. No. 4,737,410. Other useful adhesives are described in U.S. Pat. Nos. 3,389,827, 4,112,213, 4,310,509, and 4,323,557.

Another class of suitable pressure sensitive adhesive is siloxane-based adhesives. The terms "silicone" and "siloxane" are used interchangeably herein. Siloxane-based pressure sensitive adhesives include, for example, those described in U.S. Pat. Nos. 5,527,578 and 5,858,545; and PCT Publication No. WO 00/02966. Specific examples include polydiorganosiloxane polyurea copolymers and blends thereof, such as those described in U.S. Pat. No. 6,007,914, and polysiloxane-polyalkylene block copolymers. Other examples of siloxane pressure sensitive adhesives include those formed from silanols, silicone hydrides, siloxanes, epoxides, and (meth)acrylates. When the siloxane pressure sensitive adhesive is prepared from (meth)acrylate-functional siloxanes, the adhesive is sometimes referred to as a siloxane (meth)acrylate.

The siloxane-based adhesive compositions comprise at least one siloxane elastomeric polymer and may contain other components such as tackifying resins. The elastomeric polymers include for example, urea-based siloxane copolymers, oxamide-based siloxane copolymers, amide-based siloxane copolymers, urethane-based siloxane copolymers, and mixtures thereof.

One example of a useful class of siloxane elastomeric polymers is urea-based silicone polymers such as silicone polyurea block copolymers. Silicone polyurea block copolymers include the reaction product of a polydiorganosiloxane diamine (also referred to as a silicone diamine), a diisocyanate, and optionally an organic polyamine. Suitable silicone polyurea block copolymers are represented by the repeating unit:

(I)

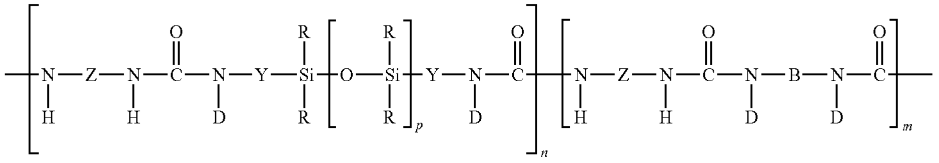

wherein each R is a moiety that, independently, is an alkyl moiety, having about 1 to 12 carbon atoms, and may be substituted with, for example, trifluoroalkyl or vinyl groups, a vinyl radical or higher alkenyl radical represented by the formula $—R^d(CH_2)_aCH{=}CH_2$ wherein the $R^d$ group is $—(CH_2)_b—$or $—(CH_2)_a CH{=}CH—$ and a is 1,2 or 3; b is 0, 3 or 6; and c is 3, 4 or 5, a cycloalkyl moiety having from about 6 to 12 carbon atoms and may be substituted with alkyl, fluoroalkyl, and vinyl groups, or an aryl moiety having from about 6 to 20 carbon atoms and may be substituted with, for example, alkyl, cycloalkyl, fluoroalkyl and vinyl groups or R is a perfluoroalkyl group as described in U.S. Pat. No. 5,028,679, or a fluorine-containing group, as described in U.S. Pat. No. 5,236,997, or a perfluoroether-containing group, as described in U.S. Pat. Nos. 4,900,474 and 5,118,775; typically, at least 50% of the R moieties are methyl radicals with the balance being monovalent alkyl or substituted alkyl radicals having from 1 to 12 carbon atoms, alkenyl radicals, phenyl radicals, or substituted phenyl radicals;

each Z is a polyvalent radical that is an arylene radical or an aralkylene radical having from about 6 to 20 carbon atoms, an alkylene or cycloalkylene radical having from about 6 to 20 carbon atoms, in some embodiments Z is 2,6-tolylene, 4,4'-methylenediphenylene, 3,3'-dimethoxy-4,4'-biphenylene, tetramethyl-m-xylylene, 4,4'-methylenedicyclohexylene, 3,5,5-trimethyl-3-methylenecyclohexylcne, 1,6-hexamethylene, 1,4-cyclohexylene, 2,2,4-trimethylhexylene and mixtures thereof;

each Y is a polyvalent radical that independently is an alkylene radical of 1 to 10 carbon atoms, an aralkylene radical or an arylene radical having 6 to 20 carbon atoms;

each D is selected from the group consisting of hydrogen, an alkyl radical of 1 to 10 carbon atoms, phenyl, and a radical that completes a ring structure including B or Y to form a heterocycle;

where B is a polyvalent radical selected from the group consisting of alkylene, aralkylene, cycloalkylene, phenylene, heteroalkylene, including for example, polyethylene oxide, polypropylene oxide, polytetramethylene oxide, and copolymers and mixtures thereof;

m is a number that is 0 to about 1000;

n is a number that is at least 1; and p is a number that is at least 10, in some embodiments 15 to about 2000, or even 30 to 1500.

Useful silicone polyurea block copolymers are disclosed in, e.g., U.S. Pat. Nos. 5,512,650, 5,214,119, 5,461,134, and 7,153,924 and PCT Publication Nos. WO 96/35458, WO 98/17726, WO 96/34028, WO 96/34030 and WO 97/40103.

Another useful class of silicone elastomeric polymers are oxamide-based polymers such as polydiorganosiloxane polyoxamide block copolymers. Examples of polydiorganosiloxane polyoxamide block copolymers are presented, for example, in US Patent Publication No. 2007-0148475. The polydiorganosiloxane polyoxamide block copolymer contains at least two repeat units of Formula II.

II

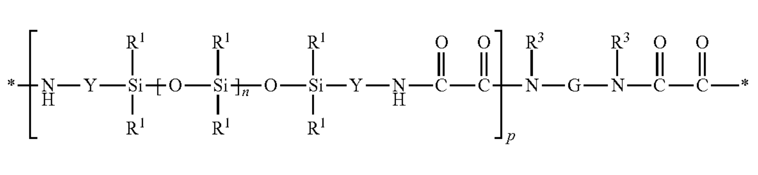

In this formula, each $R^1$ is independently an alkyl, haloalkyl, aralkyl, alkenyl, aryl, or aryl substituted with an alkyl, alkoxy, or halo, wherein at least 50 percent of the $R^1$ groups are methyl. Each Y is independently an alkylene, aralkylene, or a combination thereof. Subscript n is independently an integer of 40 to 1500 and the subscript p is an integer of 1 to 10. Group G is a divalent group that is the residue unit that is equal to a diamine of formula $R^3HN$-G-$NHR^3$ minus the two —$NHR^3$ groups. Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3HN$-G-$NHR^3$ is piperazine or the like). Each asterisk (*) indicates a site of attachment of the repeat unit to another group in the copolymer such as, for example, another repeat unit of Formula II.

Suitable alkyl groups for $R^1$ in Formula II typically have 1 to 10, 1 to 6, or 1 to 4 carbon atoms. Exemplary alkyl groups include, but are not limited to, methyl, ethyl, isopropyl, n-propyl, n-butyl, and iso-butyl. Suitable haloalkyl groups for $R^1$ often have only a portion of the hydrogen atoms of the corresponding alkyl group replaced with a halogen. Exemplary haloalkyl groups include chloroalkyl and fluoroalkyl groups with 1 to 3 halo atoms and 3 to 10 carbon atoms. Suitable alkenyl groups for $R^1$ often have 2 to 10 carbon atoms. Exemplary alkenyl groups often have 2 to 8, 2 to 6, or 2 to 4 carbon atoms such as ethenyl, n-propenyl, and n-butenyl. Suitable aryl groups for $R^1$ often have 6 to 12 carbon atoms. Phenyl is an exemplary aryl group. The aryl group can be unsubstituted or substituted with an alkyl (e.g., an alkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), or halo (e.g., chloro, bromo, or fluoro). Suitable aralkyl groups for $R^1$ usually have an alkylene group having 1 to 10 carbon atoms and an aryl group having 6 to 12 carbon atoms. In some exemplary aralkyl groups, the aryl group is phenyl and the alkylene group has 1 to 10 carbon atoms, 1 to 6 carbon atoms, or 1 to 4 carbon atoms (i.e., the structure of the aralkyl is alkylene-phenyl where an alkylene is bonded to a phenyl group).

At least 50 percent of the $R^1$ groups are methyl. For example, at least 60 percent, at least 70 percent, at least 80 percent, at least 90 percent, at least 95 percent, at least 98 percent, or at least 99 percent of the $R^1$ groups can be methyl. The remaining $R^1$ groups can be selected from an alkyl having at least two carbon atoms, haloalkyl, aralkyl, alkenyl, aryl, or aryl substituted with an alkyl, alkoxy, or halo.

Each Y in Formula II is independently an alkylene, aralkylene, or a combination thereof. Suitable alkylene groups typically have up to 10 carbon atoms, up to 8 carbon atoms, up to 6 carbon atoms, or up to 4 carbon atoms. Exemplary alkylene groups include methylene, ethylene, propylene, butylene, and the like. Suitable aralkylene groups usually have an arylene group having 6 to 12 carbon atoms bonded to an alkylene group having 1 to 10 carbon atoms. In some exemplary aralkylene groups, the arylene portion is phenylene. That is, the divalent aralkylene group is phenylene-alkylene where the phenylene is bonded to an alkylene having 1 to 10, 1 to 8, 1 to 6, or 1 to 4 carbon atoms. As used herein with reference to group Y, "a combination thereof" refers to a combination of two or more groups selected from an alkylene and aralkylene group. A combination can be, for example, a single aralkylene bonded to a single alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

Each subscript n in Formula II is independently an integer of 40 to 1500. For example, subscript n can be an integer up to 1000, up to 500, up to 400, up to 300, up to 200, up to 100, up to 80, or up to 60. The value of n is often at least 40, at least 45, at least 50, or at least 55. For example, subscript n can be in the range of 40 to 1000, 40 to 500, 50 to 500, 50 to 400, 50 to 300, 50 to 200, 50 to 100, 50 to 80, or 50 to 60.

The subscript p is an integer of 1 to 10. For example, the value of p is often an integer up to 9, up to 8, up to 7, up to 6, up to 5, up to 4, up to 3, or up to 2. The value of p can be in the range of 1 to 8, 1 to 6, or 1 to 4.

Group G in Formula II is a residual unit that is equal to a diamine compound of formula $R^3HN$-G-$NHR^3$ minus the two amino groups (i.e., —$NHR^3$ groups). Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3HN$-G-$NHR^3$ is piperazine). The diamine can have primary or secondary amino groups. In most embodiments, $R^3$ is hydrogen or an alkyl. In many embodiments, both of the amino groups of the diamine are primary amino groups (i.e., both $R^3$ groups are hydrogen) and the diamine is of formula $H_2N$-G-$NH_2$.

In some embodiments, G is an alkylene, heteroalkylene, polydiorganosiloxane, arylene, aralkylene, or a combination thereof. Suitable alkylenes often have 2 to 10, 2 to 6, or 2 to 4 carbon atoms. Exemplary alkylene groups include ethylene, propylene, butylene, and the like. Suitable heteroalkylenes are often polyoxyalkylenes such as polyoxyethylene having at least 2 ethylene units, polyoxypropylene having at least 2 propylene units, or copolymers thereof. Suitable polydiorganosiloxanes include the polydiorganosiloxane diamines of Formula II, which are described above, minus the two amino groups. Exemplary polydiorganosiloxanes include, but are not limited to, polydimethylsiloxanes with alkylene Y groups. Suitable aralkylene groups usually contain an arylene group having 6 to 12 carbon atoms bonded to an alkylene group having 1 to 10 carbon atoms. Some exemplary aralkylene groups are phenylene-alkylene where the phenylene is bonded to an alkylene having 1 to 10 carbon atoms, 1 to 8 carbon atoms, 1 to 6 carbon atoms, or 1 to 4 carbon atoms. As used herein with reference to group G, "a combination thereof" refers to a combination of two or more groups selected from an alkylene, heteroalkylene, polydiorganosiloxane, arylene, and aralkylene. A combination can be, for example, an aralkylene bonded to an alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

The polydiorganosiloxane polyoxamide tends to be free of groups having a formula —$R^a$—(CO)—NH— where $R^a$ is an alkylene. All of the carbonylamino groups along the backbone of the copolymeric material are part of an oxalylamino group (i.e., the —(CO)—(CO)—NH—group). That is, any carbonyl group along the backbone of the copolymeric material is bonded to another carbonyl group and is part of an oxalyl group. More specifically, the polydiorganosiloxane polyoxamide has a plurality of aminoxalylamino groups.

The polydiorganosiloxane polyoxamide is a linear, block copolymer and is an elastomeric material. Unlike many of the known polydiorganosiloxane polyamides that are generally formulated as brittle solids or hard plastics, the polydiorganosiloxane polyoxamides can be formulated to include greater than 50 weight percent polydiorganosiloxane segments based on the weight of the copolymer. The weight percent of the diorganosiloxane in the polydiorganosiloxane polyoxamides can be increased by using higher molecular weight polydiorganosiloxanes segments to provide greater than 60 weight percent, greater than 70 weight percent, greater than 80 weight percent, greater than 90 weight percent, greater than 95 weight percent, or greater than 98 weight percent of the polydiorganosiloxane segments in the polydiorganosiloxane polyoxamides. Higher amounts of the polydiorganosiloxane can be used to prepare elastomeric materials with lower modulus while maintaining reasonable strength.

Some of the polydiorganosiloxane polyoxamides can be heated to a temperature up to 200° C., up to 225° C., up to 250° C., up to 275° C., or up to 300° C. without noticeable degradation of the material. For example, when heated in a thermogravimetric analyzer in the presence of air, the copolymers often have less than a 10 percent weight loss when scanned at a rate 50° C. per minute in the range of 20° C. to about 350° C. Additionally, the copolymers can often be heated at a temperature such as 250° C. for 1 hour in air without apparent degradation as determined by no detectable loss of mechanical strength upon cooling.

The polydiorganosiloxane polyoxamide copolymers have many of the desirable features of polysiloxanes such as low glass transition temperatures, thermal and oxidative stability, resistance to ultraviolet radiation, low surface energy and hydrophobicity, and high permeability to many gases. Additionally, the copolymers exhibit good to excellent mechanical strength.

Another useful class of silicone elastomeric polymer is amide-based silicone polymers. Such polymers are similar to the urea-based polymers, containing amide linkages (—N(D)—C(O)—) instead of urea linkages (—N(D)—C(O)—N(D)—), where C(O) represents a carbonyl group and D is a hydrogen or alkyl group.

Such polymers may be prepared in a variety of different ways. Starting from the polydiorganosiloxane diamine described above in Formula II, the amide-based polymer can be prepared by reaction with a poly-carboxylic acid or a poly-carboxylic acid derivative such as, for example di-esters. In some embodiments, an amide-based silicone elastomer is prepared by the reaction of a polydiorganosiloxane diamine and dimethyl salicylate of adipic acid.

An alternative reaction pathway to amide-based silicone elastomers utilizes a silicone di-carboxylic acid derivative such as a carboxylic acid ester. Silicone carboxylic acid esters can be prepared through the hydrosilation reaction of a silicone hydride (i.e. a silicone terminated with a silicon-hydride (Si—H) bonds) and an ethylenically unsaturated ester. For example a silicone di-hydride can be reacted with an ethylenically unsaturated ester such as, for example, $CH_2{=}CH{-}(CH_2)_n{-}C(O){-}OR$, where C(O) represents a carbonyl group and n is an integer up to 15, and R is an alkyl, aryl or substituted aryl group, to yield a silicone chain capped with $-Si-(CH_2)_{n+2}-C(O)-OR$. The —C(O)—OR group is a carboxylic acid derivative which can be reacted with a silicone diamine, a polyamine or a combination thereof. Suitable silicone diamines and polyamines have been discussed above and include aliphatic, aromatic or oligomeric diamines (such as ethylene diamine, phenylene diamine, xylylene diamine, polyoxalkylene diamines, etc).

Another useful class of silicone elastomeric polymer is urethane-based silicone polymers such as silicone polyurea-urethane block copolymers. Silicone polyurea-urethane block copolymers include the reaction product of a polydiorganosiloxane diamine (also referred to as silicone diamine), a diisocyanate, and an organic polyol. Such materials are structurally very similar to the structure of Formula I except that the —N(D)—B—N(D)— links are replaced by —O—B—O— links. Examples are such polymers are presented, for example, in U.S. Pat. No. 5,214,119.

These urethane-based silicone polymers are prepared in the same fashion as the urea-based silicone polymers except that an organic polyol is substituted for an organic polyamine. Typically, since the reaction between a alcohol group and an isocyanate group is slower than the reaction between a amine group and an isocyanate group, a catalyst such as a tin catalyst commonly used in polyurethane chemistry, is used.

Among the particularly suitable siloxane-based pressure sensitive adhesive layers are those that include polydiorganosiloxane polyoxamide copolymers prepared by the methods described in U.S. Pat. No. 8,765,881 (Hays et al.). This method includes providing an oxalylamino-containing compound and then reacting the oxalylamino-containing compound with a silicone-based amine. The oxalylamino-containing compound is of Formula III.

III

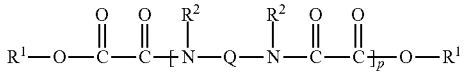

In this formula, each $R^1$ group is independently an alkyl, haloalkyl, aralkyl, substituted aralkyl, alkenyl, aryl, substituted aryl, or imino of formula $-N{=}CR^4R^5$. Each $R^4$ is hydrogen, alkyl, aralkyl, substituted aralkyl, aryl, or substituted aryl. Each $R^5$ is an alkyl, aralkyl, substituted aralkyl, aryl, or substituted aryl. Each $R^2$ is independently hydrogen, alkyl, aralkyl, aryl, or part of a heterocyclic group that includes Q and the nitrogen to which $R^2$ is attached. Group Q is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and a nitrogen to which $R^2$ is attached, or (e) a combination thereof. The variable p is an integer equal to at least 1. The silicone-based amine that is reacted with the oxalylamino-containing compound has a polydiorganosiloxane segment and at least two primary amino groups, at least two secondary amino groups, or at least one primary amino group plus at least one secondary amino group. The resulting polydiorganosiloxane polyoxamide copolymers have the same general formula as Formula II above, where the G groups in Formula II correspond to Q groups in Formula III.

Another class of siloxane-based adhesives are those developed to be gentle to the skin. A variety of gentle-to-skin articles and dressings that use gentle-to-skin adhesives have been described. A gentle-to-skin adhesive is described in US Patent Publication No. 2011/0212325 (Determan et al.) which describes an electron beam and gamma radiation crosslinked silicone gel adhesive that may use either non-functional or functional poly diorganosiloxanes. These adhesives are gel adhesives that comprise a crosslinked matrix and siloxane fluid.

In some embodiments, the siloxane-based pressure sensitive adhesive further comprises a siloxane tackifying resin. Siloxane tackifying resins have in the past been referred to as "silicate" tackifying resins, but that nomenclature has been replaced with the term "siloxane tackifying resin". The siloxane tackifying resins are added in sufficient quantity to achieve the desired tackiness and level of adhesion. In some embodiments, a plurality of siloxane tackifying resins can be used to achieve desired performance.

Suitable siloxane tackifying resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary siloxane resins include MQ siloxane tackifying resins, MQ siloxane tackifying resins are copolymeric resins where each M unit is bonded to a Q unit, and each Q unit is bonded to at least one other Q unit. Some of the Q units are bonded to only other Q units. However, some Q units are bonded to hydroxyl radicals resulting in $HOSiO_{3/2}$ units (i.e., "TOH" units), thereby accounting for some silicon-bonded hydroxyl content of the siloxane tackifying resin.

Suitable siloxane tackifying resins are commercially available from sources such as Dow Corning (e.g., DC 2-7066), Momentive Performance Materials (e.g., SR545 and SR1000), and Wacker Chemie AG (e.g., BELSIL TMS-803).

Typically, the pressure sensitive adhesive layer is a continuous layer, but in some embodiments the pressure sensitive adhesive layer is a discontinuous layer. In some embodiments, the pressure sensitive adhesive layer is present in a pattern. The pressure sensitive adhesive can have a variety of thicknesses, typically the layer is from 25-100 micrometers (1-4 mils) in thickness.

One suitable class of pressure sensitive adhesives bridges the two categories, in that it is both (meth)acrylate-based and siloxane-based. These adhesives are siloxane-(meth)acrylate copolymers. A wide range of siloxane-(meth)acrylate copolymers are suitable. Typically, the siloxane-(meth)acrylate copolymer is the reaction product of a reaction mixture comprising at least one ethylenically unsaturated siloxane-containing macromer, at least one alkyl (meth)acrylate monomer, and optional additional monomers. A particularly suitable method of preparing siloxane-(meth)acrylate copolymers is described in US Patent Publication No. 2011/0300296, which describes preparing the copolymers under essentially adiabatic polymerization conditions. Such polymerizations can be carried out without the use of solvent or with a minimum of solvent.

In this polymerization method, a wide variety of ethylenically unsaturated siloxane-containing monomers may be used. For example, a number of vinyl-functional siloxanes are commercially available. Particularly suitable are siloxane-containing macromers, especially ones with the general formula of Formula IV:

$$W-(A)_n-Si(R^4)_{3-m}Q_m \quad \text{Formula IV}$$

where W is a vinyl group, A is a divalent linking group, n is zero or 1, m is an integer of from 1 to 3; $R^4$ is hydrogen, lower alkyl (e.g., methyl, ethyl, or propyl), aryl (e.g., phenyl or substituted phenyl), or alkoxy, and Q is a monovalent siloxane polymeric moiety having a number average molecular weight above about 500 and is essentially unreactive under copolymerization conditions.

Such macromers are known and may be prepared by the method disclosed by Milkovich et al., as described in U.S. Pat. Nos. 3,786,116 and 3,842,059. The preparation of polydimethylsiloxane macromer and subsequent copolymerization with vinyl monomers have been described in several papers by Y. Yamashita et al., Polymer J. 14, 913 (1982); ACS Polymer Preprints 25 (1), 245 (1984); Makromol. Chem. 185, 9 (1984) and in U.S. Pat. No. 4,693,935 (Mazurek). This method of macromer preparation involves the anionic polymerization of hexamethylcyclotrisiloxane monomer to form living polymer of controlled molecular weight, and termination is achieved via chlorosilane compounds containing a polymerizable vinyl group.

The ethylenically unsaturated siloxane-containing monomer can be reacted with a wide range of (meth)acrylate monomers. (Meth)acrylate monomers have been described above. Examples of suitable (meth)acrylate monomers include, but are not limited to, benzyl methacrylate, n-butyl acrylate, n-butyl methacrylate, cyclohexyl acrylate, cyclohexyl methacrylate, decyl acrylate, 2-ethoxy ethyl acrylate, 2-ethoxy ethyl methacrylate, ethyl acrylate, 2-ethylhexyl acrylate, ethyl methacrylate, n-hexadecyl acrylate, n-hexadecyl methacrylate, hexyl acrylate, hydroxy-ethyl methacrylate, hydroxy ethyl acrylate, isoamyl acrylate, isobornyl acrylate, isobornyl methacrylate, isobutyl acrylate, isodecyl acrylate, isodecyl methacrylate, isononyl acrylate, isooctyl acrylate, isooctyl methacrylate, isotridecyl acrylate, lauryl acrylate, lauryl methacrylate, 2-methoxy ethyl acrylate, methyl acrylate, methyl methacrylate, 2-methyl butyl acrylate, 4-methyl-2-pentyl acrylate, 1-methylcyclohexyl methacrylate, 2-methylcyclohexyl methacrylate, 3-methylcyclohexyl methacrylate, 4-methylcyclohexyl methacrylate, octadecyl acrylate, octadecyl methacrylate, n-octyl acrylate, n-octyl methacrylate, 2-phenoxy ethyl methacrylate, 2-phenoxy ethyl acrylate, propyl acrylate, propyl methacrylate, n-tetradecyl acrylate, n-tetradecyl methacrylate, and mixtures thereof.

The pressure sensitive adhesive may further comprise one or more optional additives, as long as the additives do not interfere with the optical or other desirable properties of the pressure sensitive adhesive layer. Among the suitable additives are antimicrobial agents. US Patent Application Publications 2018/0280591 and 2015/0238444, disclose antimicrobial agents dispersed throughout an adhesive composition. For example, chlorohexidine gluconate can be included within the pressure-sensitive acrylate adhesive to provide continuous antimicrobial activity.

In some embodiments, the optically transparent tape further comprises a transparent reinforcing material layer with a first major surface and a second major surface wherein the transparent reinforcing material layer is located between the transparent tape backing and the optically transparent pressure sensitive adhesive layer. Typically, at least a portion of the second major surface of the optically transparent pressure sensitive adhesive layer is in contact with the first major surface of the transparent material layer and the second major surface of the transparent material layer is in contact with at least a portion of the first major surface of the transparent tape backing.

The reinforced tape, like the tapes described above, are optically transparent. Like the tapes described above, the reinforced transparent tape is capable of forming an optically transparent multi-layer tape stack comprising at least 2 layers of tape.

A wide range of reinforcing material layers are suitable. Typically, the optically transparent reinforcing material layer is less extensible than the optically transparent backing. For example, the reinforcing material layer can have a tensile strength from 100 to 300 Newtons/5 centimeters in the machine direction and from 100-300 N/5 cm in the cross-web direction. For example, the reinforcing material layer can have an elongation from 20-30% in the machine direction and from 15-30% in the cross-web direction. To allow for the overall reinforced tape to be flexible and conformable, the reinforcing material layer typically is flexible and conformably in the x-y plane, or in other words is drapable. In some embodiments, the reinforcing material layer is a polymeric material that is thermoformable or thermoplastic. Examples of suitable materials for the reinforcing material layer include polyurethanes, polyesters, and polyolefins.

In some embodiments, the reinforcing material layer comprises a web of polymeric materials or a discontinuous layer comprising a polyester, or a polyolefin. In some embodiments, the reinforcing material layer is a grid, wherein up to 70% of the reinforcing material is open area. An example of a suitable material for use as the reinforcing material layer is a cross laminated polyolefin open mesh nonwoven web. For example, CLAF fabric is suitable as the reinforcing material.

The reinforcing material layer is typically fairly thin relative to the thickness of the tape backing. Generally, the reinforcing material layer has a thickness from 100 to 300 micrometers.

The transparent tape, whether it is a reinforced tape or not, may also have an optional LAB coating on the backside of the optically transparent tape backing. In tape applications, a release material is often referred to as a "low adhesion backsize," or LAB. In this form, the adhesive surface contacts the back surface of the article. The LAB prevents the adhesive from permanently adhering to the back surface of the article and allows that article to be unwound. A wide range of LAB coatings are suitable, depending upon the composition of the pressure sensitive adhesive, and as long as the coating does not adversely affect the optical properties of the tape article. Examples of various low adhesion backsizes are found in U.S. Pat. Nos. 4,421,904, 4,313,988, and 4,279,717.

Also disclosed herein are multi-layer articles comprising a substrate surface, and a multi-layer tape stack disposed on the substrate surface. The multi-layer tape stack comprises at least 2 layers, a first layer and a second layer, of optically transparent tape. The optically transparent tapes are described above. Typically, the first layer of optically transparent tape comprises an optically transparent tape backing with a first major surface and a second major surface, and an optically transparent pressure sensitive adhesive layer with a first major surface and a second major surface, where at least a portion of the second major surface of the optically transparent pressure sensitive layer is adjacent to at least a portion of the first major surface of the optically transparent tape backing. The tape is optically transparent and has a moisture vapor transmission rate (MVTR) of at least 250 $g/m^2/24$ hrs/37° C./100-10% RH using the inverted cup method. The first major surface of the optically transparent pressure sensitive adhesive layer is in contact with the substrate surface. The second layer of the optically transparent tape is adhered to the first layer of optically transparent tape such that the first major surface of the optically transparent pressure sensitive adhesive layer of the second layer of optically transparent tape is disposed on the second major surface of the optically transparent tape backing of the first optically transparent tape. The multi-layer tape stack is optically transparent.

Typically, the substrate surface comprises mammalian skin. Mammalian skin is well understood in the art as the skin of the mammal, frequently a human being, to which the adhesive tape is attached. In some embodiments, the mammalian skin is treated prior to attachment by shaving, clipping, washing or the like, while in other embodiments the article is attached without preparation.

In some embodiments, the multi-layer tape stack further comprises a third layer of the optically transparent tape adhered to the second layer of optically transparent tape such that the first major surface of the optically transparent pressure sensitive adhesive layer of the third layer of optically transparent tape is disposed on the second major surface of the optically transparent tape backing of the second optically transparent tape, wherein the multi-layer tape stack is optically transparent. Additional layers of optically transparent tape can be added to form a multi-layer tape stack with 4, 5, or even more layers.

In some embodiments, the optically transparent tape can be a reinforced optically transparent tape as described above.

The multi-layer tape stack may be used to hold a medical device in place on the substrate surface. In these embodiments, the multi-layer tape stack is in contact with at least a portion of the medical device as well as to the substrate surface. Examples of medical devices that are held in place with tapes include drapes, tubing, catheters, ostomy appliances, and sensors. Additional uses for medical tapes include a wide variety of applications where tape is applied to the skin of a patient. Examples include holding a patient to an operating or treatment table, covering a part of a patient such as holding eyes closed during surgery, or immobilizing a hand during surgery to the hand, or to overlay a wound closure, not as a wound dressing but to hold the wound closed especially when the wound is closed with staples or sutures.

Also disclosed herein are methods of adhering a medical device to mammalian skin. In some embodiments, the method comprises providing a substrate surface comprising mammalian skin, providing a medical device to be adhered to the mammalian skin, placing the medical device adjacent to the substrate surface, providing an optically transparent tape, contacting a first portion of the optically transparent tape to the medical device and a portion of the substrate surface, and over-taping the first portion of optically transparent tape. Over-taping comprises contacting a second portion of the optically transparent tape to the first portion of optically transparent tape, to form a tape stack of optically transparent tape, wherein the tape stack is optically transparent. In some embodiments, the method further comprises over-taping with additional portions of optically transparent tape. As mentioned above, a wide range of medical devices are suitable. Examples of medical devices that are held in place with tapes include drapes, tubing, catheters, ostomy appliances, and sensors. Additional uses for medical tapes include a wide variety of applications where tape is applied to the skin of a patient. Examples include holding a patient to an operating or treatment table, covering a part of a patient such as holding eyes closed during surgery, or immobilizing a hand during surgery to the hand, or to overlay a wound closure, not as a wound dressing but to hold the wound closed especially when the wound is closed with staples or sutures.

The optically transparent tape used in the methods of this disclosure comprise the optically transparent tapes described above. In some embodiments, the optically transparent tape comprises a reinforced optically transparent tape as described above.

The present disclosure may be understood by reference to the Figures. FIG. 1 shows a cross-sectional view of optically transparent tape 100. Tape 100 comprises optically transparent backing layer 110 and optically transparent pressure sensitive adhesive layer 120.

Figure 2:
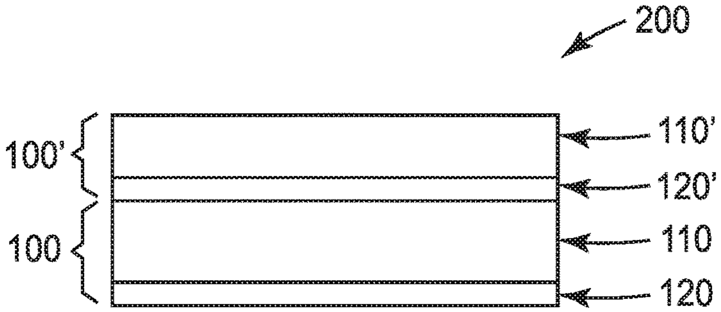
FIG. 2 is a cross-sectional view of a multi-layer tape stack article of this disclosure.

FIG. 2 shows a cross-sectional view of multi-layer tape stack 200. Tape stack 200 comprises two portions of optically transparent tape 100 shown in FIG. 1 above in contact with each other. Optically transparent tape 100 comprises transparent backing layer 110 and optically transparent pressure sensitive adhesive layer 120. Optically transparent tape 100' comprises transparent backing layer 110' and optically transparent pressure sensitive adhesive layer 120'.

Figure 3:
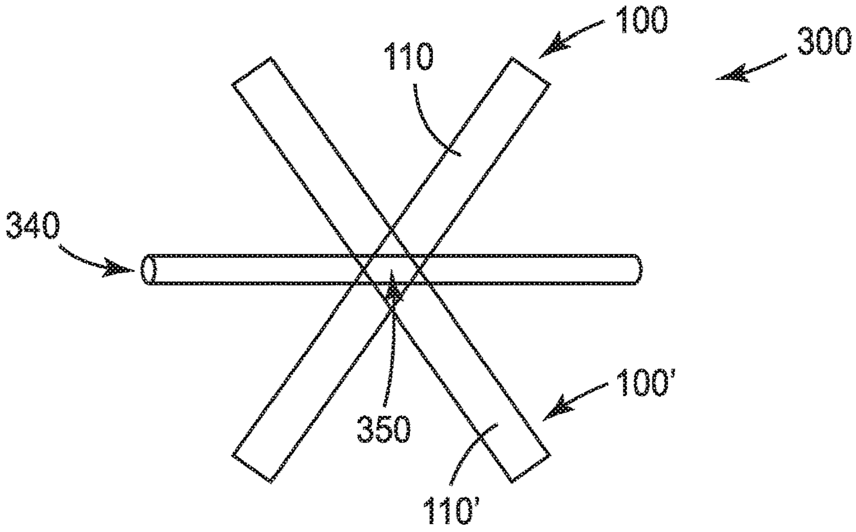
FIG. 3 is a top view of a multi-layer tape stack article of this disclosure.

FIG. 3 shows a top view of multi-layer article 300. Article 300 includes medical device 340 (shown as tubing), and optically transparent tape 100 and optically transparent tape 100' with visible backing surfaces 110 and 110' respectively. Over-tape region 350 is where optically transparent tape 100' is in contact with optically transparent tape 100. As will be clear to one of skill in the art, medical device 340 could be a wide range of medical devices, and over-tape region 350 need not be the result of a crisscross taping pattern but can encompass a broad range of over-tape regions.

Figure 4:
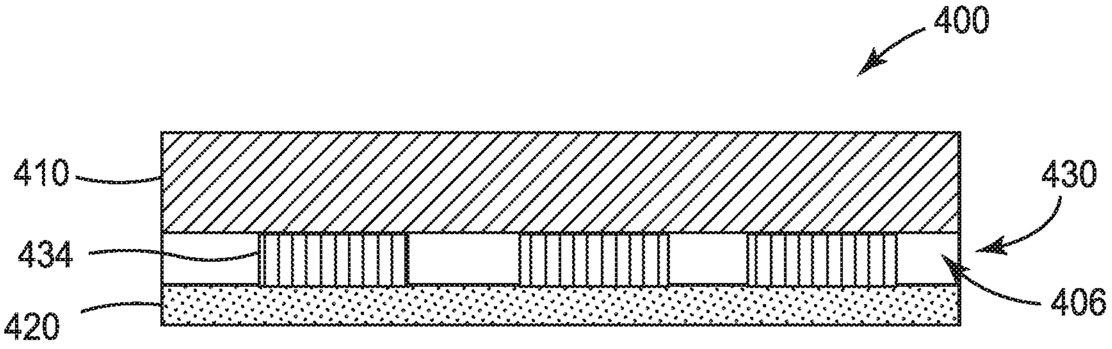
FIG. 4 is cross-sectional view of a reinforced tape article of this disclosure.

FIG. 4 shows a cross-sectional view reinforced optically transparent tape article 400. Reinforced tape 400 comprises optically transparent tape backing 410, optically transparent pressure sensitive adhesive layer 420, and reinforcing material layer 430 located between optically transparent tape backing 410 and optically transparent pressure sensitive adhesive layer 420. Optically transparent reinforcing layer comprises fibers 434 and open space 406.

Figure 5:
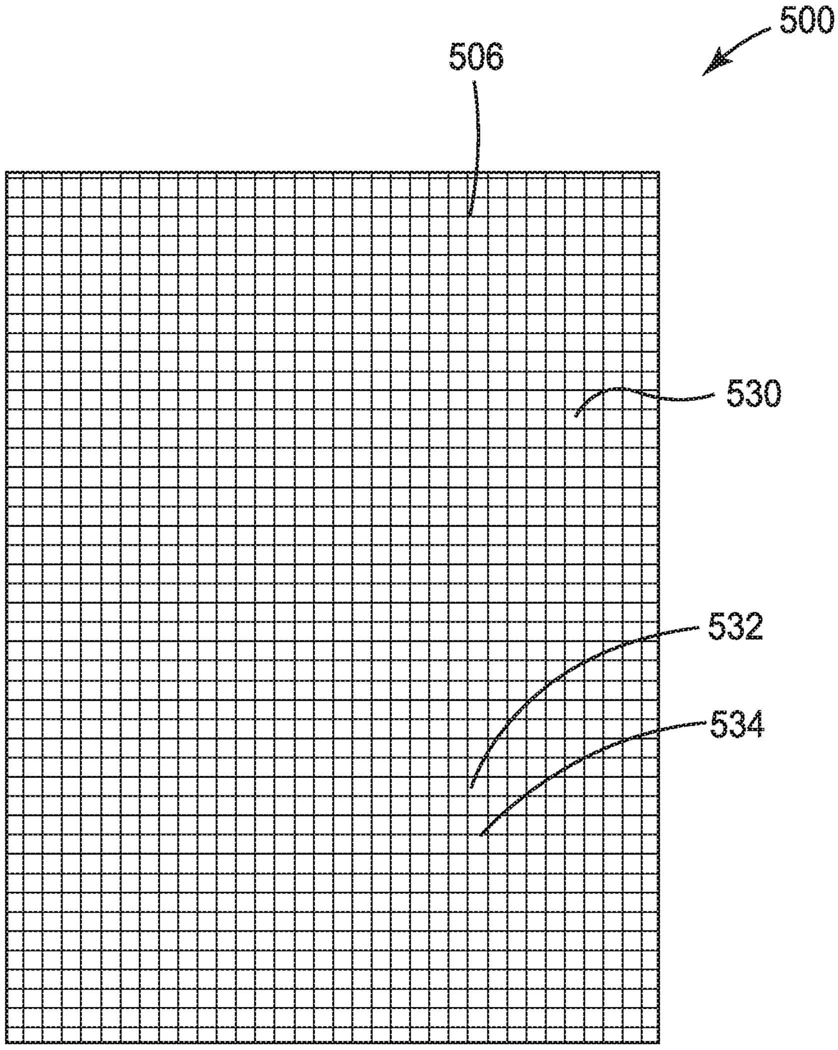
FIG. 5 is a top view of a reinforcing web layer of this disclosure.

FIG. 5 shows a top view of optically transparent reinforcing web 500. Reinforcing web 500 includes interwoven optically transparent fibers 532 and 534 and open spaces 506.

Figure 6:
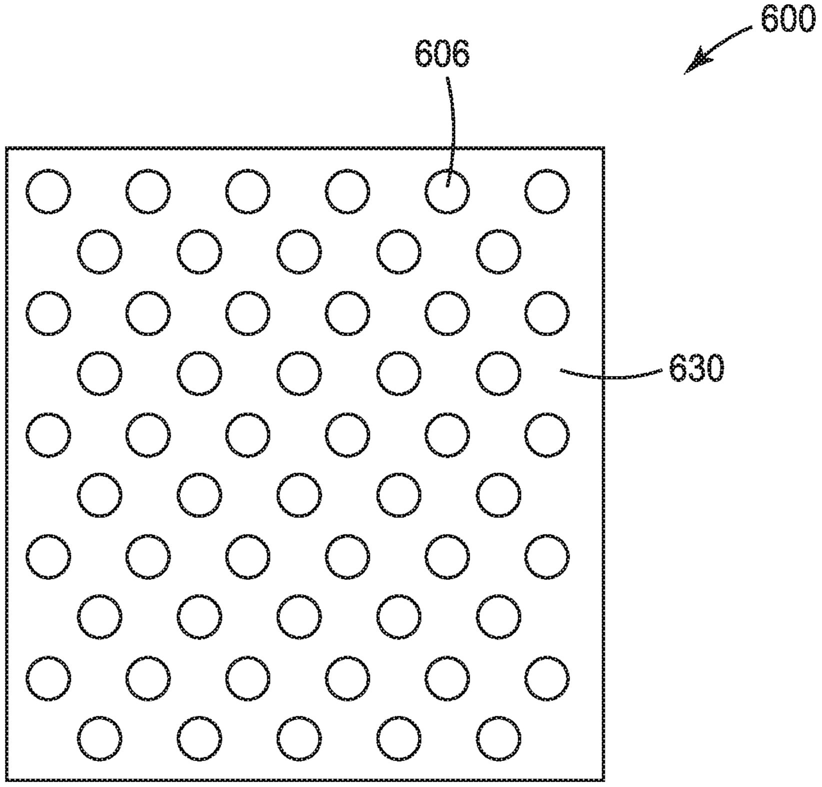
FIG. 6 is a top view of another reinforcing web layer of this disclosure.

FIG. 6 shows a top view of optically transparent reinforcing layer 600. Reinforcing layer 600 includes optically transparent film 630 and comprising a plurality of void spaces 606.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wisconsin unless otherwise noted. The following abbreviations are used: cm=centimeters; in=inch; kg=kilograms; lb=pounds; N m=Newton meters; m1=milliliters; oz=ounces; mJ=milliJoules.

TABLE 1

Materials.

| Material Identifier | Description | Source (Location) |
|---|---|---|
| Reference Tape 1 | BLENDERM medical tape | 3M Company (St. Paul, MN) |
| Reference Tape 2 | TRANSPORE medical tape | 3M Company (St. Paul, MN) |
| Film 1 | SBOPP film | Simultaneously biaxially oriented polypropylene formed as describe in US Patent Publication No. 2004/0184150 |
| Film 2 | polyolefin open mesh nonwoven material "CLAF SS 1601" | JX Nippon ANCI, Inc. (Kennesaw, GA) |

Test Methods

Optical Properties

Luminous transmission, clarity and haze were measured according to ASTM D1003-00 using a Gardner Haze-Guard Plus model 4725 (available from BYK-Gardner, Columbia, MD). Values reported are the average of three replicates unless noted otherwise. A Swiss glass microscope slide was used as a blank in the testing. One, two, and four layers of tape were tested. Each lamination (to the glass slide or tape to tape) was performed using two passes of a four-pound roller.

Mechanical properties

Tensile strength at break and ultimate elongation at break were conducted according to a method modified from PSTC-31, ASTM D882, and D3759 test methods using a Z005 Tensile Tester with clamp-type jaws (Zwick Roell Group, Kennesaw, Georgia, USA) at a constant rate of 25.4 cm/minute.

Samples were cut into 2.54 cm by 2.54 cm squares. One end of the sample square was aligned and clamped to the upper jaw contact line with the sample length being perpendicular to the upper jaw, then the other end of the sample was gently aligned and clamped to the lower jaw while applying no tension to the sample. The crosshead was then started, and the test was continued until the sample ruptured or broke. The tensile strength at break and ultimate elongation at break were recorded automatically by the instrument. The reported values are the average of five replicates unless noted otherwise.

Peel Adhesion

Samples were cut to dimensions of 2.54 centimeters by 12.7 centimeters. The liner was removed from the sample and the sample placed adhesive side down on a #320 stainless steel or a polyethylene test panel. The sample was secured to the test panel using two passes of a 2.0 kg steel roller. The peel test was carried out using a Z005 Tensile Tester (Zwick Roell Group, Kennesaw, Georgia, USA) equipped with a 50 kg load cell at room temperature with a separation rate of 30.5 centimeters/minute. The average peel force was recorded and used to calculate the average peel adhesion strength in ounces/inch. The reported values are the average of five replicates unless noted otherwise. The adhesion strength in ounces/inch were converted to Newtons/decimenter (N/dm).

Moisture Vapor Transmission Rate (MVTR)

Test samples were prepared by cutting discs having diameters of 3.8 cm from the bulk film. Each disc was placed between two foil rings with elliptical openings, thus exposing a sample surface area of 5.1 $cm^2$ and forming a foil/dressing/foil assembly (the "assembly"). The reported values are the average of five replicates unless noted otherwise.

To test upright MVTR, 50 ml of deionized water was placed inside a 4-oz. jar. One or two drops of methylene blue mixture (0.17% wt/wt methylene blue aqueous solution) were added to the jar as a visual aid to detect sample leakage. An assembly was placed on the rubber washer ring over the bottle mouth with the adhesive surface of the assembly facing downward toward the interior of the jar. The jar was placed in a chamber at a temperature of 40° C.±1° C. and 20% relative humidity for four hours. A sealing ring having a circular opening in its center, the opening having a diameter of 1.5 in. (3.8 cm), was tightened onto the jar mouth while the jar was inside the chamber to secure the assembly to the jar. The jar was removed from the chamber and weighed immediately; the mass was recorded as $W_1$. The jar was returned to the chamber for a minimum of eighteen hours (the "test period"), then the jar was removed from the chamber and immediately reweighed; this mass measurement recorded as $W_2$. The time the jar is in the chamber after measuring $W_1$, i.e., the test period, was recorded as T. The upright MVTR is calculated using Formula I below:

$$\frac{MVTR = (W1 - W2)4.74\times 10^4}{T(\text{hours})\ \text{minimum } 18} \qquad \text{Formula I}$$

$W1$ = initial weight (grams)

$W2$ = final weight (grams)

$T$ = time (hours)

where:

$W_1$ is the mass of bottle before test period;

$W_2$ is the mass of bottle after test period; and

T is the test period in hours.

Sample Preparation

Two commercially available medical tapes were used as controls: Reference Tape 1 (BLENDERM) and Reference Tape 2 (TRANSPORE), both available from 3M Company (St. Paul, MN). The two Example tape samples of the invention were designed to be optically transparent. Optical measurements for these comparative tapes are shown in Table 2.

Example 1

Film 2 (CLAF SS 1601) is a cross laminated polyolefin open mesh nonwoven material that is available from 7X Nippon ANCI, Inc. (Kennesaw, GA). The adhesive used was a hot melt processable (meth)acrylate PSA of isooctyl acrylate and acrylic acid (approximately 96/4 monomer ratio) prepared as described in U.S. Pat. No. 6,294,249 (Hamer et al.). The adhesive was extruded onto a release liner and the Film 2 nonwoven material was then applied to the adhesive. The adhesive was applied at a rate that provided a coating weight of 5.6 grains/24 $in^2$. The polyurethane film used in TEGADERM was then laminated to the adhesive/Film 3 construction. Optical measurements for this tape are shown in Table 2.

Example 2

A medical-grade acrylic pressure sensitive adhesive was coated onto a release liner at a rate that provided a coating weight of about 6 grains/24 $in^2$. The adhesive was a cross-linkable (meth)acrylate PSA of 2-ethylhexyl acrylate, n-butyl acrylate, acrylic acid, and ABP, prepared as described in U.S. Pat. No. 5,637,646 (Ellis). ABP refers to a copolymerizable photoinitiator of 4-acryloxy benzophenone, prepared according to U.S. Pat. No. 4,737,559 (Kellen et al.). The adhesive layer was subsequently UV cured with UV dose of 52-55 $mJ/cm^2$.

Clear Film 1 (SBOPP) was then laminated to the adhesive, and the laminate was flame perforated to provide improved MVTR and easy hand tearing. The laminate was perforated using a flame perforation process as described in PCT Pub. Nos. WO 2009/014881 (Strobel, et al.), WO 2015/100319 (Strobel, et al.), and WO 2016/105501 (Hager, et al.). In this process, the laminate was passed over a chilled roller having an array of cavities while a flame was used to apply heat to the web surface. The laminate was oriented with the SBOPP film layer of the laminate contacting the chilled roller. The release liner was removed before use. Optical measurements for this tape are shown in Table 2. Additionally, Peel and MVTR measurements are presented in Tables 3 and 4 respectively.

TABLE 2

Optical Properties

| Sample | % T | % H | % C |
|---|---|---|---|
| Microscope slide (Swiss glass) | 93.2 | 3.4 | 99.8 |
| 3M TRANSPORE 3" (One layer) | 84.9 | 79.5 | 19.9 |
| 3M TRANSPORE 3" (Two layers) | 79.7 | 88.9 | 23.5 |
| 3M TRANSPORE 3" (Four layers) | 70.9 | 97.3 | 5.57 |
| 3M BLENDERM 1" (One layer) | 86.9 | 89.2 | 4.69 |
| 3M BLENDERM 1" (Two layers) | 84.6 | 92.2 | 4.37 |
| 3M BLENDERM 1" (Four layers) | 79.8 | 95.4 | 4.09 |
| Example 1 (One layer) | 87.4 | 39.0 | 54.4 |
| Example 1 (Two layers) | 81.3 | 62.2 | 29.9 |
| Example 1 (Four layers) | 72.6 | 85.3 | 13.8 |
| Example 2 (One layer) | 89.6 | 32.7 | 64.8 |
| Example 2 (Two layers) | 90.5 | 51.3 | 46.2 |
| Example 2 (Four layers) (Two replicates) | 81.4 | 74.8 | 23.3 |

TABLE 3

Peel and MVTR data.

| | Peel force from 320 SS Average in Ounces/inch(N/dm) | Moisture Vapor Transmission Rate (grams/$m^2$ · 24 hours) |
|---|---|---|
| Example 2 | 20.5 (22.4) | 5080 |

TABLE 4

Ultimate tensile strength and elongation of Example 2.

| | Tensile ($lb_f$) N m | Elongation (%) |
|---|---|---|
| Example 2 | (8.6) 11.7 | 44.1 |

What is claimed is:

1. A tape comprising:

an optically transparent tape backing with a first major surface and a second major surface; and an optically transparent pressure sensitive adhesive layer with a first major surface and a second major surface, wherein at least a portion of the second major surface of the optically transparent pressure sensitive adhesive layer is adjacent to at least a portion of the first major surface of the optically transparent tape backing, wherein the tape is optically transparent having:

a % Transmission of visible light of at least 85%, a haze of less than 40%, and a clarity of at least 50%, wherein the optically transparent tape has a moisture vapor transmission rate (MVTR) of at least 250 $g/m^2$/24 hrs/37° C./100-10% RH using the inverted cup method, and wherein the optically transparent tape is capable of forming an optically transparent multi-layer tape stack comprising at least 2 layers of optically transparent tape, formed by over-taping the optically transparent tape with a second piece of the optically transparent tape, the optically transparent multi-layer tape stack having:

a % Transmission of visible light of at least 80%, a haze of less than 70%, and a clarity of at least 30%.

2. The tape of claim 1, wherein the optically transparent tape backing comprises a polyester, a polyolefin, or a polyurethane.

3. The tape of claim 1, wherein the optically transparent pressure sensitive adhesive layer comprises a (meth) acrylate-based pressure sensitive adhesive, a silicone pressure sensitive adhesive, a (meth) acrylate-silicone pressure sensitive adhesive, or a silicone gel adhesive.

4. The tape of claim 1, further comprising a transparent reinforcing material layer with a first major surface and a second major surface wherein the transparent reinforcing material layer is located between the optically transparent tape backing and the optically transparent pressure sensitive adhesive layer such that at least a portion of the second major surface of the optically transparent pressure sensitive adhesive layer is in contact with the first major surface of the transparent reinforcing material layer and the second major surface of the transparent reinforcing material layer is in contact with at least a portion of the first major surface of the optically transparent tape backing.

5. The tape of claim 4, wherein the transparent reinforcing material layer comprises a web of polymeric materials or a discontinuous layer comprising a polyester, or a polyolefin.

6. The tape of claim 4, wherein the transparent reinforcing material layer is a grid, wherein up to 70% of the transparent reinforcing material layer is open area.

7. The tape of claim 4, wherein the transparent reinforcing material layer has a thickness from 100 to 300 micrometers.

8. A tape comprising:

an optically transparent tape backing with a first major surface and a second major surface; and an optically transparent pressure sensitive adhesive layer with a first major surface and a second major surface, wherein at least a portion of the second major surface of the optically transparent pressure sensitive adhesive layer is adjacent to at least a portion of the first major surface of the optically transparent tape backing; and a transparent reinforcing material layer with a first major surface and a second major surface wherein the transparent reinforcing material layer is located between the optically transparent tape backing and the optically transparent pressure sensitive adhesive layer such that at least a portion of the second major surface of the optically transparent pressure sensitive adhesive layer is in contact with the first major surface of the transparent reinforcing material layer and the second major surface of the transparent reinforcing material layer is in contact with at least a portion of the first major surface of the optically transparent tape backing, wherein the tape is optically transparent and has a moisture vapor transmission rate (MVTR) of at least 250 $g/m^2$/24 hrs/37° C./100-10% RH using the inverted cup method, and wherein the tape is capable of forming an optically transparent multi-layer tape stack comprising at least 2 layers of tape.

* * * * *